United States Patent [19]

Johal et al.

[11] Patent Number: 4,954,440

[45] Date of Patent: Sep. 4, 1990

[54] PRODUCTION OF POLYSACCHARIDES FROM FILAMENTOUS FUNGI

[75] Inventors: Sarjit S. Johal, Sagamore Hills; Howard A. Cash, Cleveland Heights, both of Ohio

[73] Assignee: The Standard Oil Company, Cleveland, Ohio

[21] Appl. No.: 436,108

[22] Filed: Nov. 13, 1989

Related U.S. Application Data

[63] Continuation of Ser. No. 207,695, Jun. 16, 1988, abandoned.

[51] Int. Cl.$^5$ .................... C12P 19/04; C12N 11/00; C12N 1/14; C07H 1/00
[52] U.S. Cl. .................................... 435/101; 435/174; 435/176; 435/813; 435/819; 435/254; 435/911; 536/1.1; 536/114
[58] Field of Search ............... 435/101, 174, 176, 813, 435/819, 254, 911; 536/114, 1.1

[56] References Cited

U.S. PATENT DOCUMENTS

| | | | |
|---|---|---|---|
| 3,028,314 | 8/1960 | Means et al. | 435/813 |
| 3,396,082 | 8/1968 | Davis et al. | 435/911 |
| 3,436,311 | 2/1966 | Ferguson et al. | 435/119 |
| 3,822,187 | 7/1974 | DuChaffaut et al. | 435/813 |
| 3,856,626 | 12/1974 | Clamen et al. | 435/813 |
| 3,957,580 | 5/1976 | Nelson | 435/174 |
| 4,001,090 | 1/1977 | Kalina | 435/813 |
| 4,149,936 | 4/1979 | Messing et al. | 435/176 |
| 4,202,940 | 5/1980 | Misaki et al. | 435/813 |
| 4,286,061 | 8/1981 | Messing et al. | 435/813 |
| 4,287,305 | 9/1981 | Compere et al. | 435/176 |
| 4,427,775 | 1/1984 | Chen et al. | 435/171 |
| 4,692,408 | 9/1987 | Banks et al. | 435/813 |
| 4,764,471 | 8/1988 | Ripka | 435/813 |

*Primary Examiner*—Ronald W. Griffin
*Assistant Examiner*—Pamela S. Webber
*Attorney, Agent, or Firm*—Larry W. Evans; Joseph G. Curatolo; Teresan W. Gilbert

[57] ABSTRACT

A process to produce products, in particular polysaccharides, from filamentous fungi, in an immobilized cell bioreactor wherein the fungus is fixed and adheres to the surface of a porous, non-particulate support and aqueous liquid medium is passed through the immobilized system and product containing medium is recycled or withdrawn from the system.

21 Claims, No Drawings

PRODUCTION OF POLYSACCHARIDES FROM FILAMENTOUS FUNGI

This is a continuation of co-pending application Ser. No. 07/207,695 filed June 16, 1988, now abandoned.

BACKGROUND

The invention relates to the use of filamentous fungi in an immobilized system for the production of biopolymers, in particular polysaccharides. Further, the invention relates to the use of filamentous fungi for the production of polysaccharides wherein the fungi is fixed and anchored onto the surface of a porous, non-particulate support to form an immobilized cell system.

Polysaccharides, in particular scleroglucan has been typically produced from filamentous fungi by submerged cultures in batch stirred tank fermentors. However, the high viscosity in the system which is the result of cell growth and product formation, limits the conversion efficiency of the fermentation process. As the viscosity of the fermentation system increases during the batch operation, the conversion of glucose to polysaccharides is reduced. High viscosity and biomass cause many operational problems, and results in high product costs. Thus, it is advantageous to discover new more efficient processes to produce biopolymers, in particular polysaccharides, from filamentous fungi.

Cultivation of filamentous fungi has many difficulties associated with it due to the viscosity associated with the biomass and products produced. Typical cell immobilization techniques for filamentous fungi are entrapment procedures employing calcium alginate carrageen and the like. Atkinson et al., U.S. Pat. No. 4,582,600 describes an apparatus for the growth of biomass via entrapment in a reticulate multiple support structure with substantial voidage. These typical techniques are of limited utility with filamentous fungi because in viscous fungal systems the small multiple supports become overgrown resulting in poor mass transfer in the fermentation. Further, a proportionately higher percentage of the glucose will be converted to biomass in such a system.

As a result there has been an interest in employing immobilization techniques for the production of biochemicals and transformation of biochemicals in living systems. Immobilization techniques have been used for biopolymer production from microorganisms, see U.S. Pat. No. 4,384,044. However, there has not been successful use of immobilization techniques for the production of high molecular weight biopolymers from filamentous fungi.

It has been discovered by the instant invention that the passive immobilization of filamentous fungi onto a fixed support is well-suited for the production of biopolymers. The use of a porous, non-particulate support provides a mycelial surface that is exposed to but not contained in the nutrient medium. Further, in the process of the instant invention the fungal filaments are anchored to the surface of the support and thus the viscosity contribution from the biomass is decreased and the biopolymer product is freely secreted into the medium. The overall viscosity of the system is lower than that in a non-immobilized system and there is increased cell concentration within the bioreactor leading to higher overall productivity.

It is an object of this invention to produce a biopolymer from a filamentous fungi in an immobilized cell system wherein the fungi are fixed to a support. It is another object of the instant invention to optimize growth conditions for filamentous fungi in an immobilized system. It is another object of the invention to produce polysaccharides, in particular scleroglucan from filamentous fungi in a fixed immobilized bioreactor system with decreased overall viscosity. It is another object of this invention to utilize the rigid immobilized system in batch, semi-batch and continuous fermentation models to optimize process efficiency.

These and other objects, together with the advantages over known methods shall become apparent from the specification which follows and are accomplished by the invention as herein described and claimed.

SUMMARY OF THE INVENTION

A process has been discovered whereby products made by filamentous fungi in a bioreactor are recovered.

Further, a process has been discovered to recover polysaccharides, in particular scleroglucan, from filamentous fungi wherein the fungi adhere to the surface of porous, non-particulate, inert, fixed support in an immobilized cell bioreactor system and wherein aqueous nutrient medium is passed through the immobilized cell bioreactor and wherein the polysaccharide containing medium is withdrawn from and/or recirculated through the bioreactor.

The process of the instant invention significantly reduces the viscosity of the bioreactor by immobilizing a majority of the biomass that is the filamentous fungi within the bioreactor and thus improving product recovery.

The process of the instant invention is useful in that polysaccharides produced from filamentous fungi are useful as viscosifiers, binders, thickeners and stabilizers in industrial and food applications.

DETAILED DESCRIPTION OF THE INVENTION

The process of the instant invention involves the immobilization of filamentous fungi on a fixed support for the production of products made by filamentous fungi. This process is generally applicable to filamentous fungi that produce products, in particular extracellular water soluble macromolecules, when grown under aerobic conditions in a liquid medium.

Typical filamentous fungi that are employed in the process of the instant invention belong to the genus *Sclerotium, Sclerotinia, Corticum, Helotium, Stromatinia, Claviceps* and the like. Organisms which produce polysaccharides by the process of the instant invention include but are not limited to *Sclerotium glucanicum, Sclerotium delphinii, Sclerotium coffeicolum, Schizophyllum commune, Sclerotium rolfsii, Corticium rolsii Sclerotinia gladod, Stromatinia narcissi* and the like. The organisms listed in U.S. 3,301,848 to Halleck are included as organisms to be employed in the instant invention.

Products produced by filamentous fungi using the process of the instant invention include but are not limited to biopolymers, proteins, secondary metabolites, polysaccharides and the like.

Typical polysaccharides produced by the process of the instant invention are glucans and the like. Generally, a glucan is characterized by 1-3 linked D-glycosyl units with some of the units containing side chains attached by 1-6 linkages.

Exemplary glucan products produced by the process of the instant invention include but are not limited to scleroglucan, schizophyllan and the like. Scleroglucan is produced by filamentous fungi of the genera *Sclerotium*, in particular by *Schlerotium rolfsii, Sclerotium glucanicum, Sclerotium delphinii, Sclerotium coffeicolum* and the like. Schizophyllan, an extracellular polysaccharide, is produced by fungi of the genera *Schizophyllum*, in particular by *Schizophyllum commune*. Scleroglucan and schizophyllan are characterized as follows: the polysaccharide is a linear chain of 1-3-linked D-glycosyl units with about 30 to about 35 percent of the linear chain containing single D-glycosyl units which are attached by 1-6 linkages. The average molecular weight is greater than or equal to $5 \times 10^{6}$. They are nonionic homopolysaccharides. The chains are self-associated in a triple helix arrangement. They dissolve in water to form pseudoplastic solutions. A scleroglucan or schizophyllan solution is stable in a wide pH range of about pH 1.5 to about pH 10, in a range of about 10% to about 20% salt concentrations and at temperatures from about 0° C. to about 121° C.

Conventional methods are employed in culturing filamentous fungi by the process of the instant invention. Typical cultivation methods employed for culturing the filamentous fungi by the process of the instant invention include but are not limited to batch fermentation, fed batch, semicontinuous fermentation, continuous fermentation and the like.

The bioreactor contains a fixed matrix support material housed in a vessel. The matrix is immersed into the liquid nutrient medium. The matrix contains one or more non-particulate supports for the filamentous fungi to anchor onto. The support material may be and preferably is nondegradable. The support material is non-particulate. The size of the matrix is determined practically by operational conditions of the immobilized bioreactor. It has been found that the individual components of the support matrix range from greater than or equal to about 1/16 inch to greater than or equal to 1 inch in depth, greater than or equal to 6 inch to greater than or equal to 100 feet in height and greater than or equal to 2 inches to greater than or equal to 50 feet wide. The support material maybe a rigid or a non-rigid material. The non-rigid sheets may be supported by a frame of suitable material such as wires, rods, construction angles, screens and the like which is then fixed in place. The individual non-particulate support material is fixed into the matrix and patterned in any configuration so long as they are operational, and allow media passage across the surface.

In general the pores of the support material should be greater than 0.1 mm. The pore size of the support material should be less than or equal to 250 pores/inch, and greater than or equal to 4 pores/inch, and most preferably about 10 pores/inch.

The filamentous fungi adhere to and anchor onto the support material in the bioreactor. The support is fixed. The support material is chemically and/or biologically inert under conditions of use. Suitable materials for the support include but are not limited to synthetic open pore polymers such as openore reticulate foam, polyurethane reticulate foam, nylon soil erosion control blanket, fibrous coatings, compressed fibrous material, ceramic materials, polyurethane and the like. Preferable materials are open-pore reticulate foam and polyurethane reticulate foam.

The support, housed in the vessel, is suspended in a nutrient growth medium, which is inoculated with the desired fungal organism. The inoculated, support-containing growth medium filled vessel is then incubated under appropriate conditions to provide for growth of the organism and whereby the aerated medium is continuously recirculated in the bioreactor to provide conditions for attachment and growth of the fungi. The filamentous fungi inoculated into the bioreactor interact with the fixed support matrix and become attached to and entrapped in the support. The anchored fungi grow and produce a fungal lawn on the surface of the support matrix. The liquid medium and air are passed throughout the housing so that preferably all surfaces of the support material are accessible to the flowing streams of nutrient medium and air. Mycelium are continually bathed by a stream of aerated medium of sufficient velocity to supply oxygen, nutrients and remove product biopolymer from fungal surfaces, the soluble polysaccharide product is transported out by the media stream. Following attachment and production of the polysaccharide fresh media can be added to the bioreactor. The media stream can be recirculated or processed to recover the polysaccharide product in a batch, semicontinuous or continuous manner. The polysaccharide is recovered from the medium by conventional recovery techniques. Further, the polysaccharide may be purified by conventional techniques.

The aqueous nutrient medium should provide a substrate for the production of polysaccharide by the fungi. The aqueous nutrient medium will normally contain assimilable carbon and nitrogen sources, organic materials and if required, minor organic and inorganic nutrients such as trace salts, trace elements, vitamins, amino acids and the like.

Various carbon sources are available, particularly for species of the genus Sclerotium which are not fastidious with respect to the substrate carbon for the growth of the fungi and the production of glucan. Typical carbon sources include but are not limited to glucose, maltose, galactose, sucrose, mannose, fructose, cellobiose, arabinose, xylose, lactose and the like. Glucose is the preferred carbon source. Suitable nitrogen sources include but are not limited to organic and inorganic nitrogen materials such as yeast extract, corn steep liquor, cornmeal, soybean flour, urea, peptone, gaseous ammonia, ammonium salts, casein hydrolysate, sodium nitrate and the like. Examples of inorganic nutrients include but are not limited to phosphorous, phosphates, potassium phosphate dibasic, potassium phosphate monobasic, magnesium sulfate, sodium chloride, ferrous sulfate, calcium chloride, zinc chloride, cobalt chloride, manganous sulfate, sodium phosphate dibasic and the like.

A further embodiment of this invention is the discovery that there is improved glucan synthesis in the process of the instant invention when glucose or glucose oligomers are employed in the medium in a concentration between about 1.0% to about 10.0% by weight preferably from about 2.0% to about 4.5% and most preferably from about 2.1% to about 3.5% by weight. Within these glucose concentration ranges the fungal growth is low and the production of glucan synthesized and accumulated high.

The process of the instant invention is advantageous in that a greater percentage of the substrate can be used for product synthesis and not diverted for production of biomass. The process results in decreased biomass viscosity, therefore, the product concentration is higher per unit viscosity. The filaments are anchored to the support matrix such that the polysaccharide solution is relatively free of the fungal biomass. Consequently, the overall viscosity of the system is reduced. The process makes it simpler to recover and separate the polysaccharide glucan product and also facilitates better transfer of medium nutrients to the fungi. The process of the instant invention results in higher product concentration per unit viscosity, less biomass and thus a reduction in downstream processing compared to other systems.

SPECIFIC EMBODIMENTS

The following examples further illustrate the present invention. These embodiments are presented by way of example and not by way of limitation of the scope of the invention. Further, it is understood that variations and modifications can be made by one skilled in the art without departing from the spirit and the scope of the invention.

Materials and Methods

Strain and Growth Conditions

*Sclerotium rolfsii* ATTC 15206 was maintained in stock culture as sclerotia which developed after vegetative growth on Sabourauds, Dextrose Agar plates. The sclerotia were passed into culture by an initial growth phase of about 4 days on the following medium, consisting of per liter of water, about 45 grams glucose; about 2.0 grams $NaNO_3$; about 1.0 gram $KH_2PO_4$; about 1.5 grams $MgSO_4$; and about 2.5 grams corn steep solids. This medium was used for all growth systems. The pH of the medium was about pH 4.5. The *Sclerotium rolfsii* mycelium was placed in a sterile Waring Blender with a volume of sterile medium about twice the volume of the cells and sheared for about 20 seconds on low speed. The resultant inoculum was placed in a flask to contain about ¼ or less volume to total flask volume and incubated at about 28° C. with rotary shaking at about 250 RPM for about 72 hours. At the end of the incubation period the culture was centrifuged at about 27,000Xg for about 30 min at about 20° C. The supernatant was collected and the cell pellet weighed and used for subculture of the stir tank fermentor or immobilized bioreactor at the standard rate of 8% weight/volume (hereafter "w/v").

Bioreactor and Immobilization Techniques.

Open, 10 pores per inch reticulate polyurethane foam (available from Recticel Foam Corporation, Chardon, Ohio) was used as the matrix for the passive adsorption of *S. rolfsii*. A sheet of polyurethane foam was housed firmly in a flat plate polycarbonate unit.

After placement of the foam into the assembly, the unit was bolted together and sterilized by autoclaving at about 121° C. for about 30 minutes. Sterilized inlet and outlet tubings were connected to about a 2 liter flask which served as an external medium reservoir. A pump was used to recirculate medium between the external reservoir and the flat plate assembly. The bioreactor had a volume of about 1.5 liters of medium with the foam matrix in-place. An additional 1 liter of medium was generally retained in the external reservoir.

The unit was operated in a configuration whereby the medium and the air were mixed together prior to entering the flat plate assembly and were then pumped into the flat plate assembly through inlet ports on both sides of and near the bottom of the flat plate assembly. The medium and gases were removed through outlet ports located on both sides and near the top of the assembly during recirculation.

The flat plate unit which contained fresh sterile medium was inoculated with about 8% w/v of *Sclerotium rolfsii* previously grown as described above. The flat plate unit was aerated for about 24 hours with no medium circulation for about 12 hours to about 96 hours to allow adsorption and colonization of the fungi onto the support. The bioreactor was operated at a room temperature of about 22° C. A batch of medium was circulated in the system for about 24 hours to about 48 hours and then drained and recharged with about 2.5 liter batch of fresh sterile medium. Circulation of the medium in the bioreactor system occurred at about 160 ml/min. from the bottom to the top of the flat plate unit.

In order to measure the performance of the system, the broth was sampled at least once a day. About 50 mls of broth was pipetted from the reservoir, centrifuged at about 27,000Xg for about 15 min at about 20° C. to remove any cell debris and then the broth was used to monitor substrate concentration, product concentration and viscosity.

Fermentor. The subcultured inoculum of *Sclerotium rolfsii* was prepared as described above and was added to a 2 liter Braun Biostat M fermentor vessel. Aeration was started at one volume of air to one volume of medium. Impeller speed was set at about 800 RPM. Fermentor cultures were run for about 40 hour.

Analytical Methods.

Scleroglucan dry weight. About 5 mls of centrifuged broth was acidified with about 20 microliters of concentrated hydrochloric acid. About 10 mls of acetone was then added and the solution vigorously vortexed. The precipitated scleroglucan was collected by spooling onto a glass rod and placed in a preweighed aluminum weigh boat. The samples were dried in a forced air oven at about 70° C. for about 72 hours. The samples were weighed and the scleroglucan dry weight determined as the difference in weight between the preweighed boat containing the dried sample and the boat minus the sample.

Viscosity Determination. Viscosity was determined using a Brookfield LVTD viscometer equipped with a small sample adaptor at about 25° C. About 15 ml of the centrifuged broth was poured into a sample adaptor of the viscometer which was mounted with an appropriate spindle. For each sample, readings were taken at four different spindle speeds of 60, 30, 12 and 6 revolutions per minute at about 120 spindle revolutions at about 25° C. The reading obtained with the specific spindle/speed combination were then multiplied by a Factor which is a constant and provided by Brookfield Engineering Laboratories to obtain the viscosity (cps) of the solution.

Biomass dry weight. The biomass was separated from the broth by centrifugation at about 27,000Xg for about 30 min. at about 20° C. The pelleted biomass was then placed in a forced air oven at about 70° C. for about 96 hours and then weighed. The biomass dry weight was then calculated.

Glucose determination. Glucose was determined using high performance liquid chromatography (HPLC, available from Waters, Millford, MA) equipped with a carbohydrate column and a refractive index detector at room temperature. The mobile phase consisted of about 80:20 acetonitrile:water. Samples were prepared by centrifugation to remove biomass and then a 1:2 sample to acetonitrile dilution was prepared whereby acetonitrile precipitated the glucan and then the solution was filtrated through about a 0.2 micron syringe filter. Glucose peak amounts were quantitated by comparing the area of the unknown glucose peak to a glucose calibration standard which was run and the areas stored in the integrator/printer.

Example 1

About a 8"×11"×¼" piece of about ten pore per inch reticulate polyurethane foam housed in a polycarbonate assembly was inoculated with *S. rolfsii* as described above.

Growth of the organism was good as evidenced by an increase in fungal cell mass on the matrix. During this period of growth the viscosity of the system increased slowly. As a result the viscosity of the first batch of media broth (termed reservoir) did not exceed 100 cps (at 10.3 sec$^{-1}$). When drained and replaced with fresh media (i.e., reservoir 2 through 12) the rise in viscosity was greater than that for reservoir 1. This practice of draining the reservoir and recharging the system with new media was followed for about the next 21 days. The results of two separate experiments are shown in Tables I and II. The viscosity increase for the duration of each reservoirs use is shown in Tables III and IV.

TABLE I

| RESERVOIR | HOURS | GLUCAN (gm/L) | PRODUCTIVITY (gm/L/hr) | CONSUMPTION (gm/L) | GLUCAN YIELD (gm glucan/ gm total glucose) |
|---|---|---|---|---|---|
| 1 | 72.0 | 14.82 | 0.207 | — | 0.87 |
| 2 | 66.5 | 20.47 | 0.308 | 24 | 0.51 |
| 3 | 29.5 | 22.18 | 0.752 | 22 | 0.50 |
| 4 | 25.0 | 21.10 | 0.844 | 10 | 0.53 |
| 5 | 47.0 | 28.18 | 0.600 | 18 | 0.70 |
| 6 | 42.5 | 29.93 | 0.704 | 16 | 0.75 |
| 7 | 30.0 | 24.25 | 0.808 | 10 | 0.61 |
| 8 | 24.0 | 18.12 | 0.766 | 6 | 0.45 |
| 9 | 24.0 | 17.72 | 0.736 | 8 | 0.44 |
| 10 | 42.0 | 21.44 | 0.510 | 15 | 0.54 |
| 11 | 46.5 | 23.82 | 0.510 | 16 | 0.60 |
| 12 | 54.5 | 14.76 | 0.270 | 7 | 0.87 |

TABLE II

| RESERVOIR | HOURS | GLUCAN (gm/L) | PRODUCTIVITY (gm/L/hr) | CONSUMPTION (gm/L) | GLUCAN YIELD (gm glucan/ gm total glucose |
|---|---|---|---|---|---|
| 1 | 89 | 27.81 | 0.812 | 17 | 0.62 |
| 2 | 47 | 29.96 | 0.637 | 19 | 0.67 |
| 3 | 49 | 32.91 | 0.672 | 12 | 0.73 |
| 4 | 30 | 16.47 | 0.549 | 7 | 0.37 |
| 5 | 47 | 23.50 | 0.500 | 8 | 0.52 |
| 6 | 40 | 36.23 | 0.906 | 3 | 0.81 |
| 7 | 32 | 20.53 | 0.642 | 5 | 0.46 |
| 8 | 42 | 27.45 | 0.654 | 6 | 0.61 |
| 9 | 52 | 31.50 | 0.606 | 7 | 0.70 |
| 10 | 40 | 16.68 | 0.417 | 7 | 0.37 |

TABLE III

| Sample Number | Run Time (Hours) | Viscosity (cps) | Reservoir |
|---|---|---|---|
| 1 | 24 | 17 | 1 |
| 2 | 43 | 18 | 1 |
| 3 | 48 | 21 | 1 |
| 4 | 66 | 36 | 1 |
| 5 | 72 | 43 | 1 |
| 6 | 74 | 8 | 2 |
| 7 | 89 | 27 | 2 |
| 8 | 115 | 131 | 2 |
| 9 | 139 | 193 | 2 |
| 10 | 140 | 24 | 3 |
| 11 | 148 | 36 | 3 |
| 12 | 163 | 116 | 3 |
| 13 | 168 | 121 | 3 |
| 14 | 169 | 9 | 4 |
| 15 | 188 | 51 | 4 |
| 16 | 193 | 60 | 4 |
| 17 | 194 | 10 | 5 |
| 18 | 211 | 21 | 5 |
| 19 | 217 | 31 | 5 |
| 20 | 235 | 66 | 5 |
| 21 | 240 | 77 | 5 |
| 22 | 242 | 8 | 6 |
| 23 | 259 | 49 | 6 |
| 24 | 283 | 160 | 6 |
| 25 | 284 | 28 | 7 |
| 26 | 308 | 155 | 7 |
| 27 | 313 | 171 | 7 |
| 28 | 314 | 18 | 8 |
| 29 | 331 | 95 | 8 |
| 30 | 337 | 102 | 8 |
| 31 | 338 | 17 | 9 |
| 32 | 356 | 74 | 9 |
| 33 | 361 | 78 | 9 |
| 34 | 362 | 13 | 10 |
| 35 | 379 | 45 | 10 |
| 36 | 385 | 63 | 10 |
| 37 | 403 | 130 | 10 |
| 38 | 405 | 17 | 11 |
| 39 | 431 | 74 | 11 |
| 40 | 449 | 167 | 11 |
| 41 | 450 | 12 | 12 |
| 42 | 476 | 27 | 12 |
| 43 | 480 | 36 | 12 |
| 44 | 497 | 83 | 12 |

TABLE IV

| Sample Number | Run Time (Hours) | Viscosity (cps) | Reservoir |
|---|---|---|---|
| 1 | 22 | 6 | 1 |
| 2 | 41 | 14 | 1 |
| 3 | 47 | 17 | 1 |

TABLE IV-continued

| Sample Number | Run Time (Hours) | Viscosity (cps) | Reservoir |
|---|---|---|---|
| 4 | 65 | 36 | 1 |
| 5 | 71 | 43 | 1 |
| 6 | 89 | 92 | 1 |
| 7 | 91 | 10 | 2 |
| 8 | 95 | 15 | 2 |
| 9 | 114 | 55 | 2 |
| 10 | 135 | 134 | 2 |
| 11 | 137 | 8 | 3 |
| 12 | 161 | 48 | 3 |
| 13 | 168 | 67 | 3 |
| 14 | 185 | 159 | 3 |
| 15 | 186 | 7 | 4 |
| 16 | 192 | 19 | 4 |
| 17 | 209 | 71 | 4 |
| 18 | 216 | 99 | 4 |
| 19 | 217 | 6 | 5 |
| 20 | 234 | 27 | 5 |
| 21 | 240 | 45 | 5 |
| 22 | 257 | 129 | 5 |
| 23 | 263 | 167 | 5 |
| 24 | 264 | 13 | 6 |
| 25 | 281 | 63 | 6 |
| 26 | 303 | 188 | 6 |
| 27 | 304 | 12 | 7 |
| 28 | 330 | 59 | 7 |
| 29 | 335 | 84 | 7 |
| 30 | 337 | 4 | 8 |
| 31 | 353 | 24 | 8 |
| 32 | 359 | 37 | 8 |
| 33 | 377 | 111 | 8 |
| 34 | 378 | 7 | 9 |
| 35 | 382 | 12 | 9 |
| 36 | 400 | 45 | 9 |
| 37 | 405 | 58 | 9 |
| 38 | 423 | 131 | 9 |
| 39 | 429 | 150 | 9 |
| 40 | 430 | 12 | 10 |
| 41 | 448 | 72 | 10 |
| 42 | 470 | 77 | 10 |

During this 21 day period of continuous operation, the majority of the fungal biomass remained firmly attached and adsorbed to the matrix. As a result the media broths were relatively free of cell debris and could be readily clarified by low-speed centrifugation.

Comparative Example

Fermentation was performed in a two-liter stirred tank fermentor (Braun Biostat M). The productivity, as measured by acetone precipitated glucan dry weight, results are shown in Table V, below. The average productivity was 0.302 gms/L/hr. The batch operated fermentations were 28 to 44 hours in duration when initiated with the standard 8% (w/v) *S. rolfsii* inoculum.

TABLE V

| Duration | Scleroglucan Productivity |
|---|---|
| 28 Hours | 0.21 grams/liter/hr |
| 40 Hours | 0.38 grams/liter/hr |
| 43 Hours | 0.35 grams/liter/hr |
| 44 Hours | 0.27 grams/liter/hr |

About a 8"×11"×¾" piece of about ten pore per inch reticulate polyurethane foam housed in a polycarbonate assembly was inoculated with S. *rolfsii* as described above.

About 48 hours after the initiation of recirculation, approximately 17% by volume of the medium was withdrawn and the system recharged with fresh complete media containing about 45 grams per liter glucose. About 24 hours later, another 15% by volume of the medium was withdrawn and replaced. The aforementioned methodology, of about 15% to 20% media change, was followed for the next five days. During this period, the viscosity increased to about 210 cps (at 10.3 sec1). Upon attaining this viscosity, the glucose concentration in the system was reduced from about 40 grams per liter to about 20 grams per liter by medium withdrawal and replacement with glucose-free nutrient medium. The glucose concentration was maintained at about 20 grams per liter for the next eight days. Maintenance at this glucose concentration produced a significant decline in the viscosity of the system. After reaching a low of about 11 cps (at $10.3 sec^{-1}$), the system was recharged using a concentrated glucose solution which increased the overall glucose concentration to approximately 45 grams per liter. As illustrated in Table VI below the viscosity of the system increased albeit very slowly.

It was also observed that when the glucose concentration was maintained at approximately 20 grams per liter, the amount of fungal biomass on the matrix and in the system increased. The increased biomass produced poor flow and media circulation characteristics which resulted in stagnant, isolated regions in the bioreactor assembly. When the glucose concentration was increased from about 20 to about 45 gram per liter, the growth of fungal biomass appeared decline and the viscosity of the system which is a measure of glucan synthesis increased.

TABLE VI

| Run Time (days) | Glucose Concentration (grams/liter) | Viscosity (cps) |
|---|---|---|
| 1 | 45 | 59 |
| 2 | 45 | 78 |
| 3 | 45 | 69 |
| 4 | 45 | 42 |
| 5 | 45 | 38 |
| 7 | 45 | 123 |
| 8 | 45 | 195 |
| 9 | 45 | 204 |
| 10 | 20 | 165 |
| 11 | 20 | 65 |
| 13 | 20 | 68 |
| 15 | 45 | 11 |
| 16 | 45 | 20 |
| 17 | 45 | 30 |
| 18 | 45 | 39 |
| 20 | 45 | 64 |

Example 3

The methodology and equipment used for this experiment were similar to that described above, however, the following modification was introduced. A matrix composed of two 8"×11"×⅜" reticulate polyurethane foam pieces with 10 pores per inch were glued back-to-back to a piece of polypropylene macroporous filter of the same dimensions. The polypropylene sheet in this matrix served to support the foam and provide rigidity.

After completing about a 96 hour adsorption and growth phase, the medium in the system was drained and replaced with complete medium containing about 45 grams per liter glucose. The medium in the system was then sampled at least once every twenty-four hours to monitor glucose concentration and viscosity. The glucose concentration was maintained at about 45 grams per liter by the addition of a concentrated glucose solution throughout this interval. After the ninth day of operation, growth in the unit appeared to have stabilized and broth viscosities of 250 cps (at $10.3 sec^{-1}$)

were being maintained. The glucose concentration was then adjusted and held in a range of about 27 to about 36 grams per liter glucose. About 250 to about 400 milliters of glucan-containing medium was withdrawn and replaced about every twenty-four hours; about 7 to about 12 grams per liter of glucose was consumed in about a 24 hour period. The system was operated for nine days at this glucose concentration.

After eighteen days of continuous operation, the broth in the system had attained a viscosity of greater than 450 cps (at 10.3 sec$^{-1}$). The glucose concentration was again altered, this time being increased to greater than 40 grams per liter. For the next six days the concentration of glucose was maintained at this level. During this interval the viscosity of the broth did not vary more than 10–15% from the preceding six days of operation when the glucose concentration was at about 30 grams per liter. During these six days it appeared that the biomass in the unit remained constant showing very little, if any, increase.

To determine how rapidly the adsorbed fungal biomass could synthesize glucan, as measured by an increase in viscosity, the broth in the system was drained and replaced with fresh medium containing about 30 grams per liter glucose. Upon replacement of the broth in the system the viscosity dropped to about 50 cps. But within about 24 hours the viscosity was observed to increase dramatically and within about forty-eight hours, after replacing medium, the viscosity of the broth stabilized at levels prior to replacement.

For the remainder of the experiment which lasted about eight weeks, the glucose concentration of the media was maintained in the range of about 27 to about 35 grams per liter. About 250 to about 400 milliters of glucan-containing medium were harvested about every twenty-four hours. The amount of biomass on the matrix and in the system did not appear to increase dramatically throughout the course of this trial. Problems of overgrowth on the matrix and suspended cell matter in the reservoir encountered in example 2 were not encountered under the conditions employed here.

Table VII shows the results of the experiment, and viscosity is assumed to be a measure of glucan synthesis in this system.

TABLE VII

| Run Time (days) | Glucose Concentration (cps) | Viscosity |
| --- | --- | --- |
| 6 | 45 | 245 |
| 7 | 45 | 47 |
| 8 | 45 | 90 |
| 9 | 45 | 270 |
| 10 | 30 | 322 |
| 11 | 30 | 369 |
| 12 | 30 | 313 |
| 13 | 30 | 432 |
| 14 | 30 | 354 |
| 15 | 30 | 456 |
| 16 | 30 | 422 |
| 17 | 30 | 395 |
| 19 | 30 | 373 |
| 20 | 30 | 511 |
| 21 | 45 | 412 |
| 22 | 45 | 384 |
| 23 | 45 | 359 |
| 24 | 45 | 354 |
| 25 | 45 | 396 |
| 26 | 45 | 416 |
| 27 | 30 | 45 |
| 28 | 30 | 119 |
| 29 | 30 | 247 |
| 30 | 30 | 379 |
| 31 | 30 | 358 |

TABLE VII-continued

| Run Time (days) | Glucose Concentration (cps) | Viscosity |
| --- | --- | --- |
| 32 | 30 | 379 |
| 33 | 30 | 404 |
| 34 | 30 | 358 |
| 35 | 30 | 335 |
| 36 | 30 | 283 |
| 37 | 30 | 318 |
| 42 | 30 | 196 |
| 43 | 30 | 347 |
| 44 | 30 | 366 |
| 45 | 30 | 373 |
| 49 | 30 | 384 |

We claim:

1. A process to produce a scleroglucan or schizophyllan product from a filamentous fungi comprising inoculating an immobilized cell bioreactor with a filamentous fungi, permitting the filamentous fungi to passively attach to and anchor onto a surface of a support material immersed in the bioreactor which material is porous wherein the pores are greater than 0.1 mm, non-particulate and fixed, incubating the fungi for at least 2 hours in the bioreactor while the aqueous nutrient medium is circulated throughout the bioreactor; and feeding grown the media and withdrawing the synch product containing medium from the bioreactor.

2. The process of claim 1 wherein the scleroglucan or schizophyllan containing medium is recirculated through the bioreactor and is operated in batch, fed batch, semi-batch or continuous modes.

3. The process of claim 1 wherein said filamentous fungi are selected from the genus consisting of *Sclerotium, Schizophyllum, Sclerotinia, Corticum, Helotium, Claviceps* and *Stromatinia*.

4. The process of claim 3 wherein the filamentous fungi are selected from the group consisting of *Sclerotium glucanicum, Sclerotium delphinii, Sclerotium coffeicolum, Schizophyllum commune, Sclerotium rolfsii, Corticium rolfsi Sclerorinia gladoli* and *Stromatinia narcissi*.

5. The process of claim 1 wherein the support material is the range from greater than or equal to about 1/16 inch to greater than or equal to 1 inch depth, greater than or equal to 6 inches to greater than or equal to 100 ft. in height and greater than or equal to 2 inches to greater than or equal to 50 ft. wide.

6. The process of claim 1 wherein the pore number of the support material should be less than or equal to 250 pores/inch and greater than or equal to 4 pores/inch.

7. The process of claim 1 wherein the withdrawn scleroglucan or schizophyllan is recovered and separated from the medium.

8. The process of claim 7 wherein the recovered scleroglucan or schizophyllan is purified.

9. The process of claim 1 wherein the pore size of the support material is about 10 pores/inch.

10. The process of claim 1 wherein the support material is selected from synthetic open pore polymers.

11. The process of claim 1 wherein the support material is selected from reticulate foam, polyurethane reticulate foam, nylon soil erosion control blanket, fibrous coating, compressed fibrous material, ceramic materials, polyurethane and combinations thereof.

12. The process of claim 11 wherein the support material is selected from reticulate foam and polyurethane reticulate foam.

13. The process of claim 1 wherein the aqueous medium is aerated.

14. The process of claim 1 wherein the aqueous nutrient medium contains assimilable carbon, nitrogen sources, organic materials and minor organic nutrients selected from trace elements, vitamins and amino acids.

15. The process of claim 1 wherein the aqueous nutrient medium contains about 1.0% to about 10.0% by weight of glucose.

16. The process of claim 15 wherein the aqueous nutrient medium contains about 2.0% to about 4.5% by weight of glucose.

17. The process of claim 16 wherein the aqueous nutrient medium contains about 2.1T to about 3.5% by weight of glucose.

18. A process to produce a polysaccharide from a filamentous fungi comprising inoculating an immobilized cell bioreactor with a filamentous fungi, allowing the filamentous fungi to attach to and anchor onto a surface of a support material immersed in the bioreactor which material is porous, non-particulate and fixed, incubating the fungi for at least 2 hours in the bioreactor while the aqueous nutrient medium is circulated throughout the bioreactor wherein the medium contains glucose concentration from about 2.0% to about 4.5% by weight glucose and withdrawing the polysaccharide containing medium from the bioreactor and wherein the polysaccharide produced is selected from the group consisting of scleroglucan or schizophyllan.

19. The process of claim 21 wherein the glucose concentration is from about 2.1% to about 3.5% by weight of glucose.

20. The process of claim 18 wherein the scleroglucan or schizophyllan is recovered and separated from the withdrawn medium.

21. A process to produce from a filamentous fungi consisting essentially of inoculating an immobilized cell bioreactor with a filamentous fungi, permitting the filamentous fungi to passively attach to and anchor onto a surface of a support material immersed in the bioreactor which material is porous, non-particulate and fixed, incubating the fungi for at least 2 hours in the bioreactor while the aqueous nutrient medium is circulated throughout the bioreactor; and feeding growth media and withdrawing the product containing medium from the bioreactor.

* * * * *

UNITED STATES PATENT AND TRADEMARK OFFICE
CERTIFICATE OF CORRECTION

PATENT NO. : 4,954,440
DATED : September 4, 1990
INVENTOR(S) : Johal et al

It is certified that error appears in the above-indentified patent and that said Letters Patent is hereby corrected as shown below:

On the title page, Item [75]: add "George M. Coleman"

Signed and Sealed this

Twelfth Day of October, 1993

Attest:

BRUCE LEHMAN

*Attesting Officer*   *Commissioner of Patents and Trademarks*